United States Patent
Beyer

(10) Patent No.: US 8,388,513 B2
(45) Date of Patent: Mar. 5, 2013

(54) APPARATUS FOR POSTERIOR PELVIC FLOOR REPAIR

(76) Inventor: Roger D. Beyer, Paw Paw, MI (US)

( * ) Notice: Subject to any disclaimer, the term of this patent is extended or adjusted under 35 U.S.C. 154(b) by 1151 days.

(21) Appl. No.: 12/087,550

(22) PCT Filed: Jan. 10, 2007

(86) PCT No.: PCT/US2007/000540
§ 371 (c)(1),
(2), (4) Date: Jul. 9, 2008

(87) PCT Pub. No.: WO2007/081954
PCT Pub. Date: Jul. 19, 2007

(65) Prior Publication Data
US 2009/0012353 A1    Jan. 8, 2009

Related U.S. Application Data

(60) Provisional application No. 60/757,619, filed on Jan. 10, 2006.

(51) Int. Cl.
A61F 2/00    (2006.01)
(52) U.S. Cl. .......................................................... 600/37
(58) Field of Classification Search .............. 600/29–32, 600/37; 606/151; 623/23.72
See application file for complete search history.

(56) References Cited

U.S. PATENT DOCUMENTS

| | | |
|---|---|---|
| 6,802,807 B2 | 10/2004 | Anderson et al. |
| 6,911,003 B2 | 6/2005 | Anderson et al. |
| 6,971,986 B2 | 12/2005 | Staskin et al. |
| 7,048,682 B2 | 5/2006 | Neisz et al. |
| 2002/0072694 A1 | 6/2002 | Snitkin et al. |
| 2004/0267088 A1 | 12/2004 | Kammerer |
| 2005/0245787 A1 | 11/2005 | Cox et al. |
| 2005/0250977 A1 | 11/2005 | Montpetit et al. |
| 2005/0278037 A1* | 12/2005 | Delorme et al. ........... 623/23.72 |

FOREIGN PATENT DOCUMENTS

| | | |
|---|---|---|
| EP | 1 609 439 | 12/2005 |
| WO | WO 02/38079 A2 | 5/2002 |
| WO | WO 2007/014241 A1 | 2/2007 |

OTHER PUBLICATIONS

Davila et al., "Current Concepts in Pelvic Anatomy and Reconstructive Surgery," Cleveland Journal of Medicine, Supplement 4 to vol. 72, pp. S2-S32, Dec. 2005.
Cervigni et al., "The Use of Synthetics in the Treatment of Pelvic Organ Prolapse," Current Opinion in Urology, vol. 11, pp. 429-435, 2001.

* cited by examiner

*Primary Examiner* — Christine Matthews
(74) *Attorney, Agent, or Firm* — Kagan Binder, PLLC

(57) ABSTRACT

Improved methods and apparatuses for treatment of posterior pelvic floor repair, including rectocele and related pelvic organ prolapse, are provided. A specialized mesh (3) having a shape for convenient placement to treat rectocele by providing both level 2 and level 3 support. Appropriate devices for introducing such a mesh implant are also disclosed.

7 Claims, 16 Drawing Sheets

Normal position of rectum

A rectocele is when the rectum bulges into vagina

Rectocele

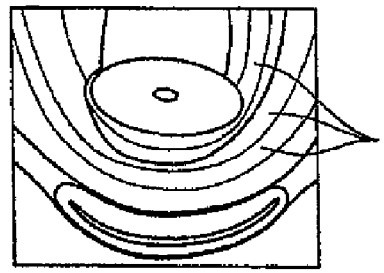
Fig. 2A — Uterosacral/cardinal ligament complex
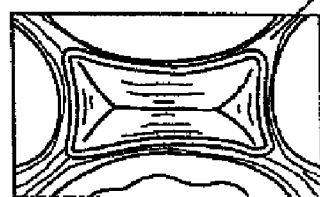
Fig. 2B — To arcus tendineus fascine pelvis; To arcus tendineus rectovaginalis
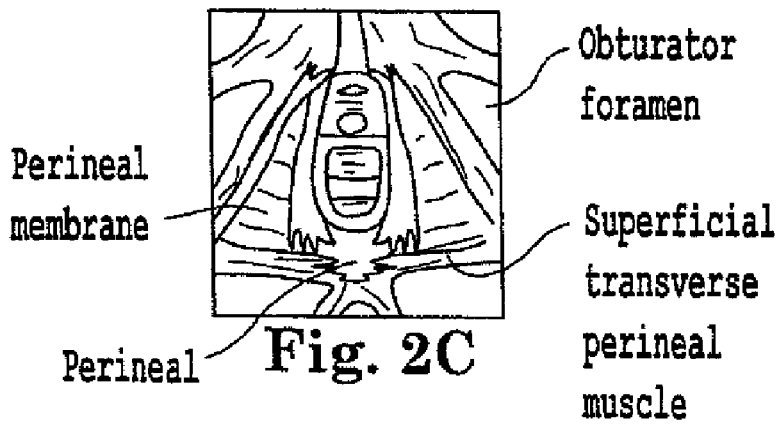
Fig. 2C — Perineal membrane; Perineal; Obturator foramen; Superficial transverse perineal muscle

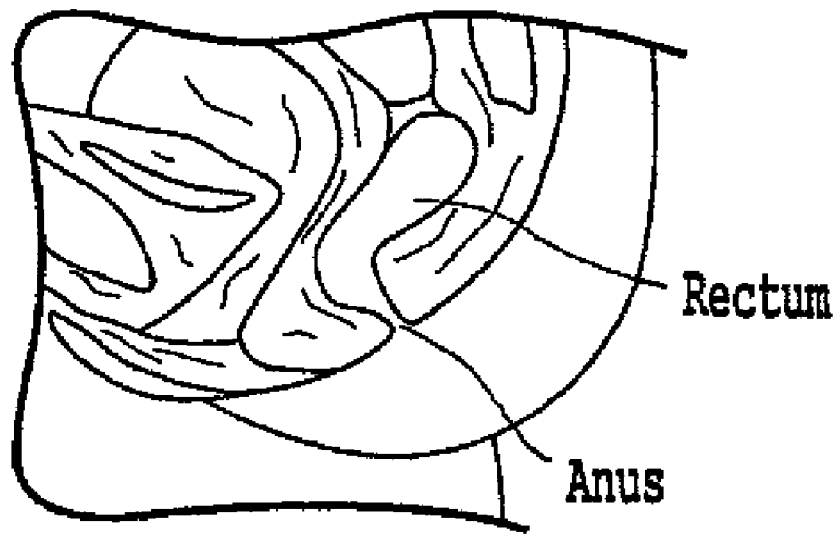
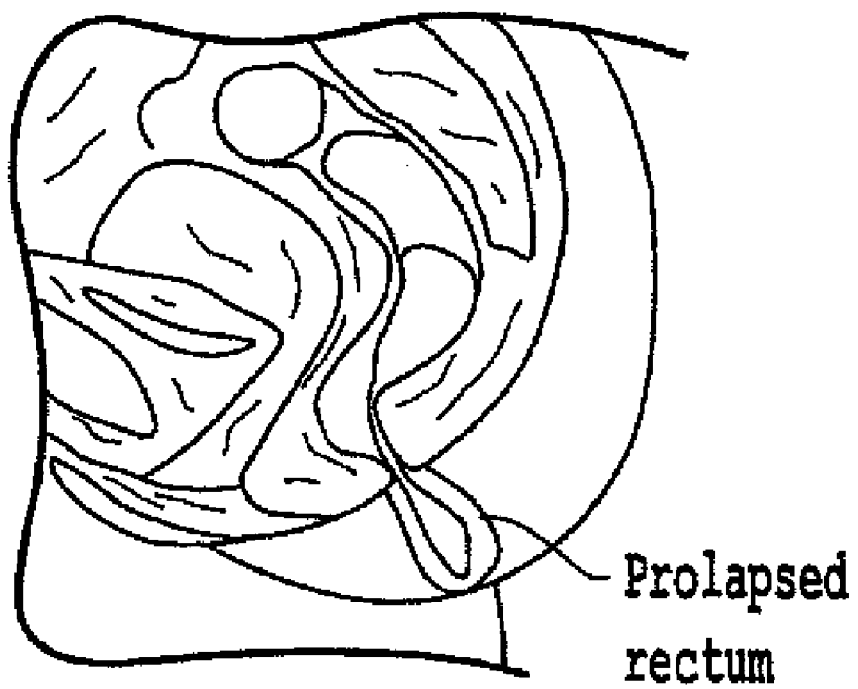
Fig. 4

Basic shape

Modified shape
(Similar to apogee)
for measurements

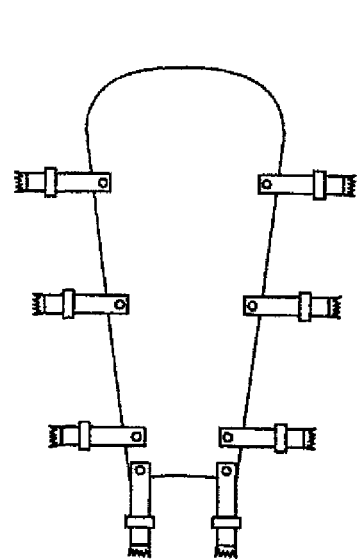
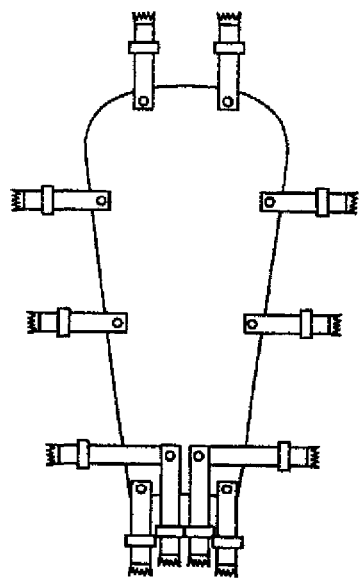
Fig. 15  Fig. 16
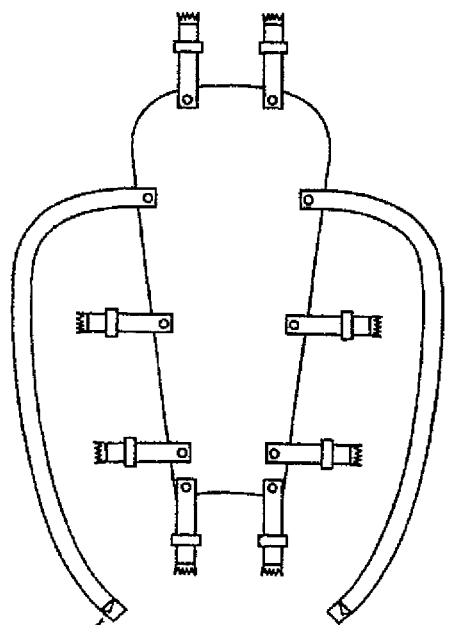
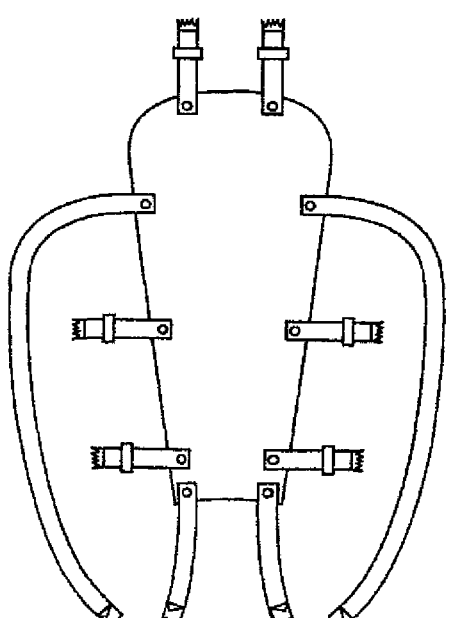
Fig. 17 — Connector  Fig. 18 — Connectors

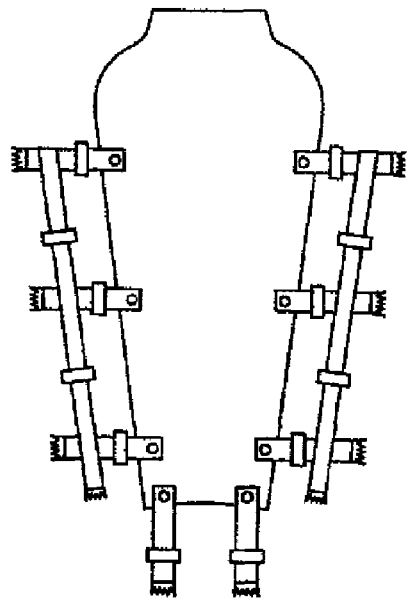
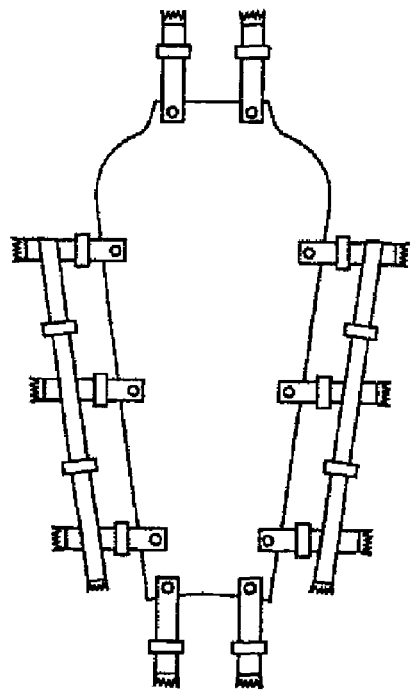
Fig. 31    Fig. 32
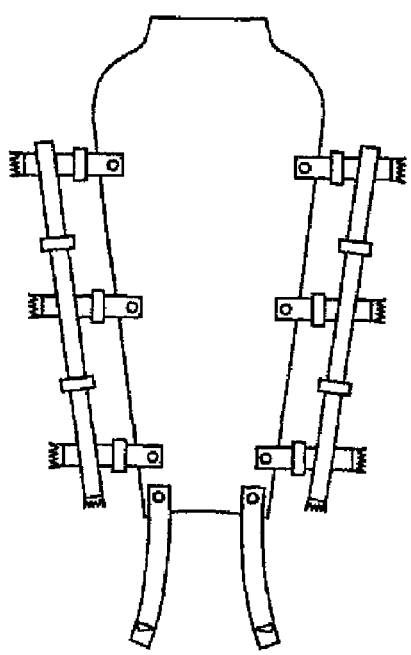
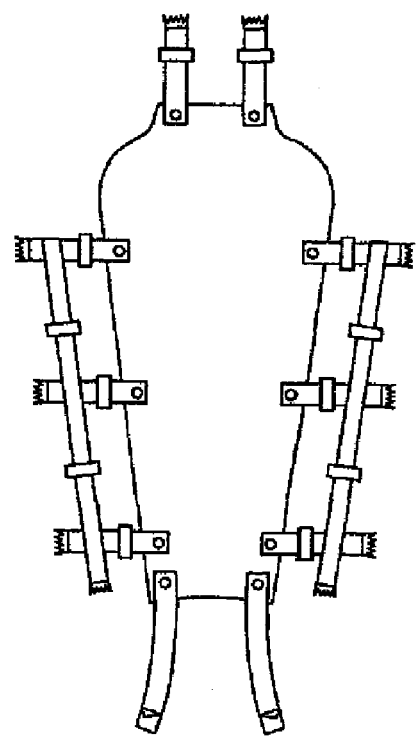
Fig. 33    Fig. 34

Fig. 35

Type 1 ARM

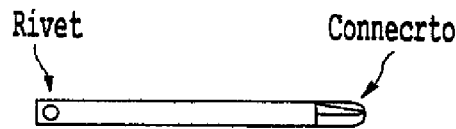

Standard with connector arm as currently on apogee – and reconnector of various lengths

Fig. 36

Type 2 ARM

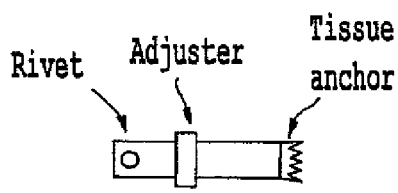

Made of poly proplane of various lengths

This Arm would come with or without adjuster

Note I adjust arm tissue anchor are the same as arm.

Reconnectable Tip same as apogee except side hole big enough to put tip of curves hemostat into tip of needle would be in far enough that when pushed back on hemostat the needle would release.

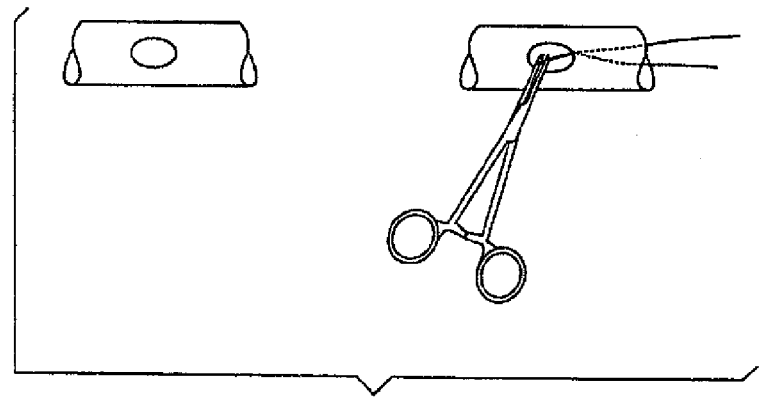

Fig. 37

Connectors instrument (needles) for upper arm more curve (flexable enough to bend with out difficulty) than apogee - as reattachable tip.

For lower arm reattachable

For tissue anchors (same as arm is)

APPARATUS FOR POSTERIOR PELVIC FLOOR REPAIR

The present non-provisional patent application claims benefit from International Application No. PCT/US2007/000540, having PCT Publication No. WO 2007/081954 A1, which was filed on Jan. 10, 2007, which in turn claims priority under 35 USC §119(e) from United States Provisional Patent Application having Ser. No. 60/757,619, filed on Jan. 10, 2006, by Roger D. Beyer, and titled APPARATUS FOR POSTERIOR PELVIC FLOOR REPAIR, wherein the entirety of said provisional patent application is incorporated herein by reference.

BACKGROUND OF THE INVENTION

1. Field of the Invention

This invention relates to urogenital and gastrointestinal surgery.

2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

The common clinical symptoms of vaginal prolapse are largely related to the fact that the vagina is inappropriately serving the role of a structural layer between intra-abdominal pressure and atmospheric pressure. This pressure differential puts tension on the supporting structures of the vagina, causing a "dragging feeling" where the tissues connect to the pelvic wall or a sacral backache due to traction on the uterosacral ligaments. Exposure of the moist vaginal walls leads to a feeling of perineal wetness and can lead to ulceration of the exposed vaginal wall. Vaginal prolapse may also result in loss of urethral support due to displacement of the normal structural relationship, resulting in stress urinary incontinence. Certain disruptions of the normal structural relationships can result in urinary retention, as well. Stretching of the bladder base is associated with vaginal prolapse and can result in complaints of increased urinary urgency and frequency. Other symptoms, such as anal incontinence and related bowel symptoms, and sexual dysfunction are also frequently seen with vaginal prolapse.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports (pubourethral ligaments and attachment of the bladder to the endopelvic fascia); central defect is caused by weakness in the central supports. There may also be a transverse defect, causing cystocele across the vagina.

Posterior vaginal wall prolapse results in descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Several factors have been implicated as being involved in genital prolapse in women. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Obesity, constipation, and a history of hysterectomy have also been implicated as possible factors.

As noted, vaginal prolapse and the concomitant anterior cystocele can lead to discomfort, urinary incontinence, and incomplete emptying of the bladder. Posterior vaginal prolapse may additionally cause defecatory problems, such as tenesmus, constipation, and anal incontinence. Furthermore, apart from the physical symptoms, vaginal prolapse has been shown to result in a lower quality of life for its sufferers, including feeling less attractive, less feminine, and less sexually attractive.

Vaginal prolapse develops when intra-abdominal pressure pushes the vagina outside the body. In a normal situation, the levator ani muscles close the pelvic floor. This results in little force being applied to the fascia and ligaments that support the genital organs. Increases in abdominal pressure, failure of the muscles to keep the pelvic floor closed, and damage to the ligaments and fascia all contribute to the development of prolapse. In addition, if a woman has a hysterectomy, the vaginal angle may be altered, causing increased pressure at a more acute angle, accelerating the prolapse.

There are generally two different types of tissue that make up the supportive structure of the vagina and uterus. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf thereby provided. It is when damage to the muscles opens the pelvic floor or during the trauma of childbirth that the fascia and ligaments are strained. Breaks in the fascia allow the wall of the vagina or cervix to prolapse downward.

Put another way, support for the pelvic structures can be described in three levels. Level 1 is the suspension of the apex of the vagina from the sides of the sacrum. The principle anatomical structure is the cardinal uterosacral ligament complex, which suspends the vagina while allowing some vertical mobility. Normally, the cervix of a woman will not descend below the plane of the ischial spines. Damage to Level 1 supports permit the uterus and upper vagina to telescope downward. Symptoms of Level 1 failure include pelvic heaviness, pressure, and urinary incontinence. A cervix-first prolapse, where the cervix inverts, is seen in complete Level 1 failure.

Level 2 concerns the lateral attachment of the vagina to the pelvic side wall. This level prevents prolapse of the bladder and the rectum into the vagina, i.e. cystocele or rectocele. The pubocervical and rectovaginal fascia provide this mid-vaginal suspensory mechanism. Level 2 support failure results in eversion of the vaginal walls, as opposed to inversion as seen in Level 1 failures. Symptoms of Level 2 failure include symptoms related to visceral failure, such as stress incontinence, voiding difficulty, fecal incontinence, or incomplete rectal evacuation. Sexual symptoms, such as painful intercourse and decreased libido are also seen.

Level 3 is near the opening of the vagina where the muscles of the levator sling and the distal portion of the vagina are joined to the perineal body. These distal vaginal defects can result from or exacerbate levator muscle flaccidity, which, if present with Level 2 failures, can result in worsening of any posterior or anterior eversion of the vagina. Level 3 failures can result in urinary and anal incontinence, and can result in vaginal dryness, chronic vaginitis, and loss of vaginal tightness due to the concomitant gaping of the lower vagina.

Level 3 support includes the perineum. The perineum is the entirety of the pelvic outlet inferior to the pelvic floor. The area between the vagina and anus is called the perineal body. The borders of the female perineum are the ischiopubic rami, ischial tuberosities, sacrotuberous ligaments and coccyx. A line connecting the ischial tuberosities divides the perineum into the urogenital triangle anteriorly and the anal triangle posteriorly. In the standing position the perineal body is oriented horizontally. The urogenital triangle is oriented horizontally and tilted upward so that it faces more anteriorly while the anal triangle is tilted upward so that it faces more posteriorly.

The perineal membrane is a thick fibrous sheet that spans the urogenital triangle. It attaches laterally to the pubic arch and has a free posterior margin anchored in the midline by the perineal body. The urethra and vagina penetrate through a hiatus in the perineal membrane (the urogenital hiatus) to exit at the vestibule. The perineal membrane, therefore, provides fixation of the distal urethra, distal vagina, and the perineal body to the pubic arches.

The urogenital triangle is divided into a superficial and deep perineal space by the perineal membrane. The superficial perineal space contains the superficial perineal muscles (ischiocavemosus, bulbospongiosus, superficial transverse perineal muscles), the erectile tissue of the clitoris, the vestibular bulbs, and Bartholin's glands. The deep perineal space lies deep to the perineal membrane and inferior to the levator ani muscles. Within this thin space lie the external urethral sphincter and the urethrovaginalis, compressor urethrae, and deep transverse perineal muscles. The urethrovaginalis and compressor urethrae muscles provide accessory sphincter function to the urethra. The urethrovaginalis muscle surrounds the distal urethra and vagina without passing between them and therefore acts as a sphincter to the vagina as well as to the distal urethra. The deep transverse perineal muscle, along with its superficial counterpart, serves to stabilize the position of the perineal body and inferior border of the perineal membrane.

The perineal body marks the point of convergence of the bulbospongiosus muscle, superficial and deep perinea, perineal membrane, external anal sphincter, posterior vaginal muscularis, and fibers from the puborectalis and pubococcygeus. The perineal body plays an important role in support of the distal vagina and in normal anorectal function.

The perineal body is supported centrally to the vagina. The connective tissue of the perineal body extends 2 to 4 cm cephalad from the hymenal ring along the posterior vaginal wall between the smooth muscle layers of the vagina and the rectum. This layer does not, however, extend the full length of the posterior vaginal wall. Therefore the perineal body gets more support for preventing downward movement from its lateral attachments. The perineal body is attached laterally to the ischial tuberosities. Superiorly, the support comes from the posterior lateral support of level 2. The posterior vaginal wall is attached laterally to the pelvic sidewall in a slightly more complex arrangement than the anterior vaginal wall. The distal half of the posterior vaginal wall fuses with the aponeurosis of the levator ani muscle from the perineal body along a line referred to as the arcus tendineus rectovaginalis. It converges with the arcus tendineus fasciae pelvis at a point 2 to 3 centimeters from the ischial spine and terminates at the ischial spine. Along the proximal ⅓ to ½ of the vagina, the anterior and posterior vaginal walls are both supported laterally to the arcus tendineus fasciae pelvis. Thus, in the proximal vagina, the lateral supports for the anterior and posterior vaginal wall are identical. This arrangement accounts for the H-shape of the distal vagina when viewed in cross-section and the flattened-tube configuration seen in the upper vagina. The Arcus tendineus rectovaginalis therefore gives direct support to the perineal body. Detachment of these lateral supports can lead to decent of the perineal body and prolapse of the posterior vaginal wall.

Level 3 support is also provided by the perineal membrane, the muscles of the deep perineal space, and the perineal body. These structures support and maintain the normal anatomical position of the urethra and the distal third of the vagina. At level 3, the vagina fuses with the urethra anteriorly and with the perineal body posteriorly. Disruption of the level 3 support anteriorly can result in urethral hypermobility and stress urinary incontinence. Disruption posteriorly may result in distal rectoceles and if there is detachment laterally from the ischial tuberosities with detachment of the lateral support from the arcus tendineus rectovaginalis there can also be perineal descent resulting in possible rectal prolapse and/or anal incontinence.

The vascular and nerve supply to the perineum, including the deep and superficial spaces, is provided by the pudendal neurovascular bundle. The pudental nerve innervates the striated urethral and anal sphincters in addition to the deep and superficial perineal muscles. Sensory innervation to the external genitalia also comes from the pudenal nerve. The pudendal nerve follows a complex course that originates from S2-S4 and travels behind the sacrospinous ligament just medial to the ischial spine, exiting the pelvis through the greater sciatic foramen. The nerve then enters the ischiorectal fossa through the lesser sciatic foramen and travels through the pudendal canal (Alcock's canal) on the medial aspect of the obturator internus muscles before separating into several terminal branches that terminate within the muscles and skin of the perineum. See Davila et al., Current Concepts in Pelvic Anatomy and Reconstructive Surgery, Cleveland Clinic Journal of Medicine. Supplement 4 to volume 72, December 2005, the entire contents of which are incorporated by reference.

When the perineal body becomes separated from it bilateral support attachments it will have downward movement of up to 3 to 6 cm. with increased abdominal pressure such as is generated with Valsalva for bowl movements. This movement causes the pudendal nerve to be repetitively stretched which can lead to denervation of the perineum structures. This nerve injury can be subtle and progressive. A common expression is the development of anal incontinence. When the perineal body is restabilized bilaterally the repetitive injury is prevented with the resolution of the incontinence. If the incontinence doesn't resolve then neural rehabilitative therapy may be required.

Treatment of vaginal prolapse and related conditions herein discussed is uncertain, and generally based on the symptoms of the prolapse. If symptoms are more severe, treatment is commonly by either surgery or pessary. Surgical options might include hysterectomy or by uterus-saving procedures. Such procedures may include abdominal or vaginal access routes. Sacralcolpopexy or sacrospinous fixation may be used. Anterior colporrhaphy is often utilized for treatment of anterior vaginal prolapse. In addition, methods of surgical repair using mesh or biological implants, or a combination thereof, to support the prolapsed organ in its appropriate position, have been developed, and may use either a transobturator or vaginal approach.

With regard to the rectocele, surgical treatment often includes the so-called posterior methods, better described as the anchorage of the involved tissues to the levator muscle (i.e., levator myorrhaphy). However, no matter the surgical approach, the rate of recurrence is unacceptably high, and the degree of satisfaction with the results of the surgeries is not acceptable.

The adaptation of synthetic mesh systems to support the repair of pelvic organ prolapse in women has, however, proven to result in improved results, reduced recurrences, and reduced morbidity associated with the repair. Examples of methods and apparatus useful for effecting repair of prolapse conditions include those disclosed in U.S. Publication 2005/0245787, herein expressly incorporated by reference, and in U.S. Publication 2005/0250977, also herein expressly incorporated by reference. U.S. Pat. No. 6,802,807, U.S. Pat. No. 6,911,003, U.S. Pat. No. 7,048,682, and U.S. Pat. No. 6,971,986 are also incorporated by reference.

Implants can be used to treat discrete prolapse conditions, or can be used to support the mid-urethra to relieve incontinence. However, if multiple levels of failure are present, multiple surgeries may be required. Indeed, some surgical options that show a good effect in treating certain symptoms, such as correcting the anatomical disorder and the concomitant sexual dysfunction, have a much less favorable effect in correcting obstructed defecation.

Consequently, there is a need for alternative methods and apparatus for repair of rectocele and other conditions associated with posterior pelvic floor pathology, particularly when several layers of support are desirable. Thus, the present invention is directed to providing such alternative methods and apparatus

SUMMARY OF THE INVENTION

The present invention concerns a mesh implant for repair of posterior pelvic floor disorders. Among the possible indications are treatment of rectocele, posterior enterocele, anal incontinence (flatal, mucus, liquid, or solid), rectal prolapse, and collapsing perineal body. The present invention may also be used to provide apical support and pudendal nerve stabilization. The present apparatus has the unique advantage of providing support in the case of Level 2 failures, plus Level 3 support for detached perineal bodies that are associated with flatal and stool incontinence. A preferred embodiment has the advantage of keeping the repaired pelvic floor above the line formed by connecting the two ischial spines, thereby protecting the pudendal nerve from injury.

In a preferred embodiment, an implant for repairing rectocele includes a central support portion having a plurality of arms. The central portion has an anterior and posterior end and two lateral ends opposite each other. The implant preferably comprises a first pair of arms extending laterally from about the middle to the upper third of the central support portion. The implant also preferably comprises a second pair of arms extending laterally from near the posterior end of the central support portion. The implant also preferably comprises a pair of appendages extending in a posterior direction from the posterior end of the central support portion.

The implant of the present invention may be made of a synthetic or non-synthetic material, or a combination thereof. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Commercial examples of synthetic materials include Marlex™ (polypropylene) available from Bard of Covington, R.I., Prolene™ (polypropylene), Prolene Soft Polypropylene Mesh or Gynemesh (non-absorbable synthetic surgical mesh), both available from Ethicon, of New Jersey, and Mersilene (polyethylene terphthalate) Hernia Mesh also available from Ethicon, Gore-Tex™ (expanded polytetrafluoroethylene) available from W. L. Gore and Associates, Phoenix, Ariz., and the polypropylene sling available in the SPARC™ sling system, available from American Medical Systems, Inc. of Minnetonka, Minn., Dexon™ (polyglycolic acid) available from Davis and Geck of Danbury, Conn., and Vicryl™ available from Ethicon.

Other examples of suitable materials include those disclosed in published U.S. patent application Ser. No. 2002/0072694, herein incorporated by reference. More specific examples of synthetic materials include, but are not limited to, polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-lactic acid, poly-D-L-lactic acid and polyphosphate esters. See Cervigni et al., The Use of Synthetics in the Treatment of Pelvic Organ Prolapse, Current Opinion in Urology (2001), 11: 429-435.

Other examples of suitable material for the present implant include polypropylene, or other suitable synthetic material, coated with collagen, or another suitable non-synthetic material.

In another preferred embodiment, the present invention is directed to a device for implanting an implant for the treatment of rectocele. The implanting device preferably comprises a handle and a curved needle. The curved needle preferably comprises a reattachable tip.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 shows a rectal prolapse.

FIGS. 7-34 show alternative embodiments of the implant of the present invention.

FIGS. 35 and 36 show alternative embodiments for the arms of the implant of the present invention.

FIG. 37 shows an embodiment of a re-connectable tip for the connection of the arm to the central support portion.

DETAILED DESCRIPTION OF THE PREFERRED EMBODIMENTS

Figure 1:
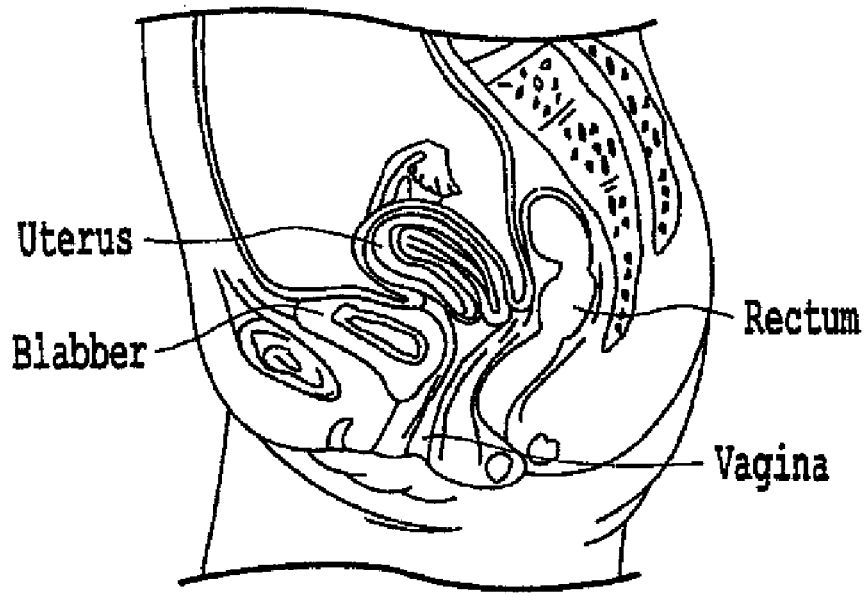
FIGS. 1 and 2 show the relevant anatomy.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

Figure 3:
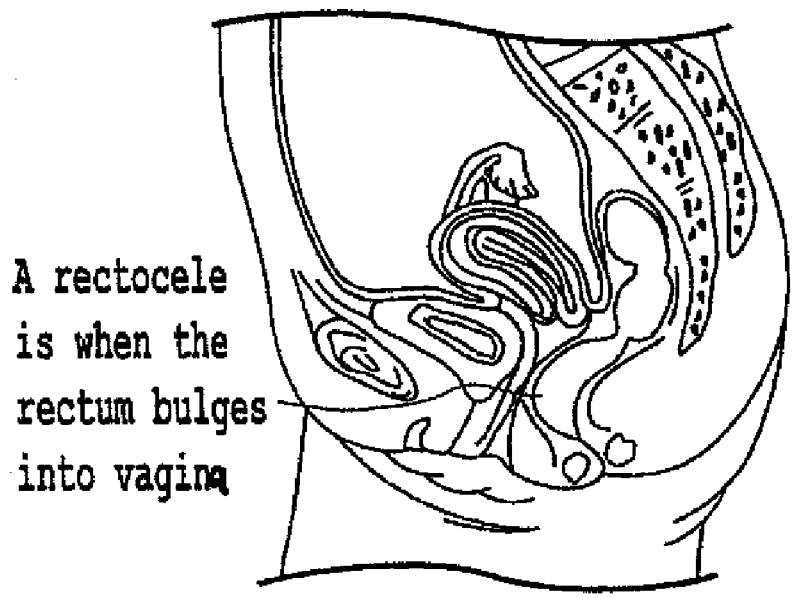
FIG. 3 shows the disrupted anatomy seen with rectocele.
Figure 2:
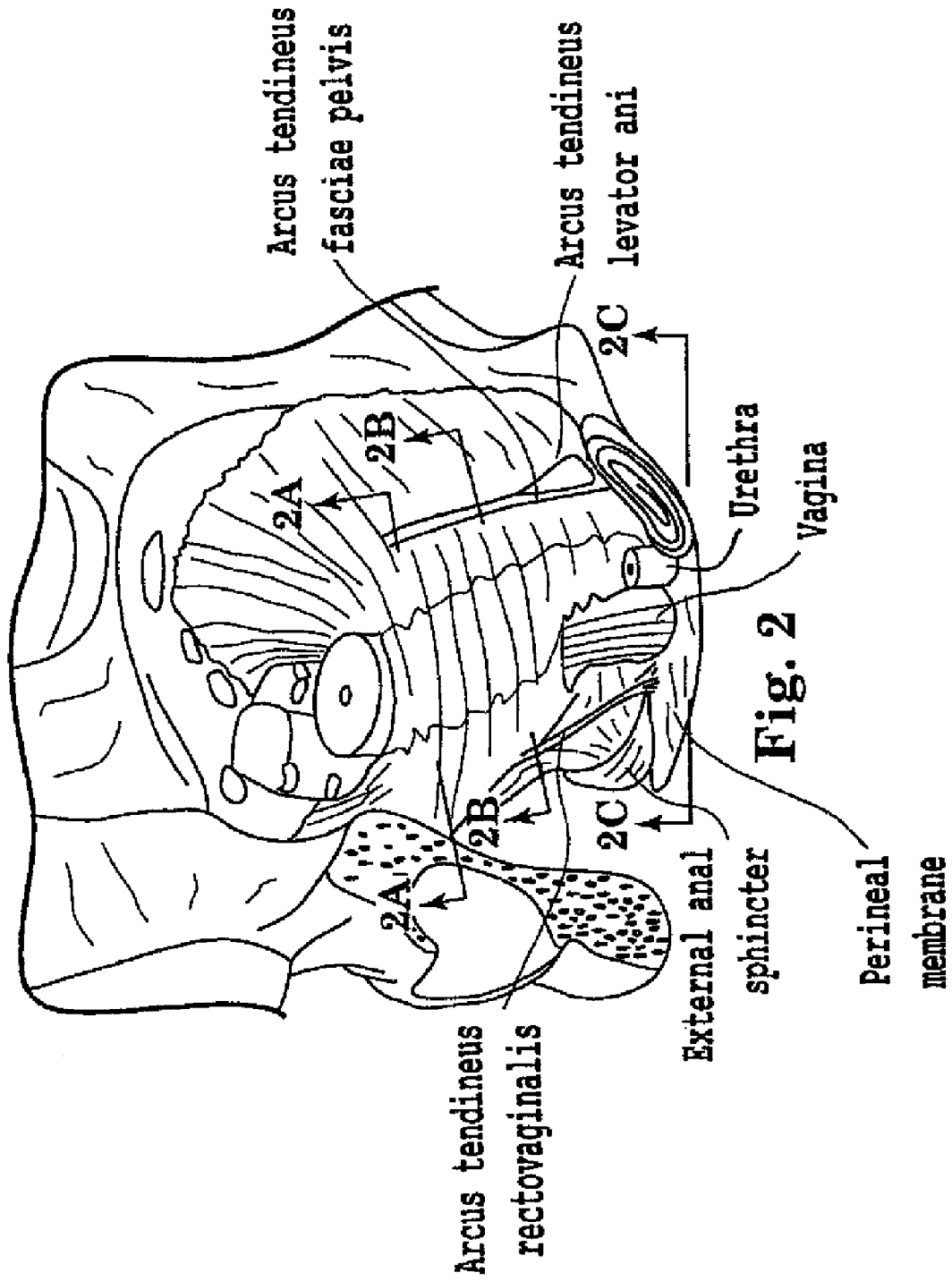

The relevant anatomy is illustrated in FIG. 1. FIG. 2 shows the various levels of support for the vagina in its normal condition. FIG. 3 shows the disrupted anatomy when the rectum bulges into the vagina in the case of rectocele. FIG. 4 shows a rectal prolapse.

Figure 5:
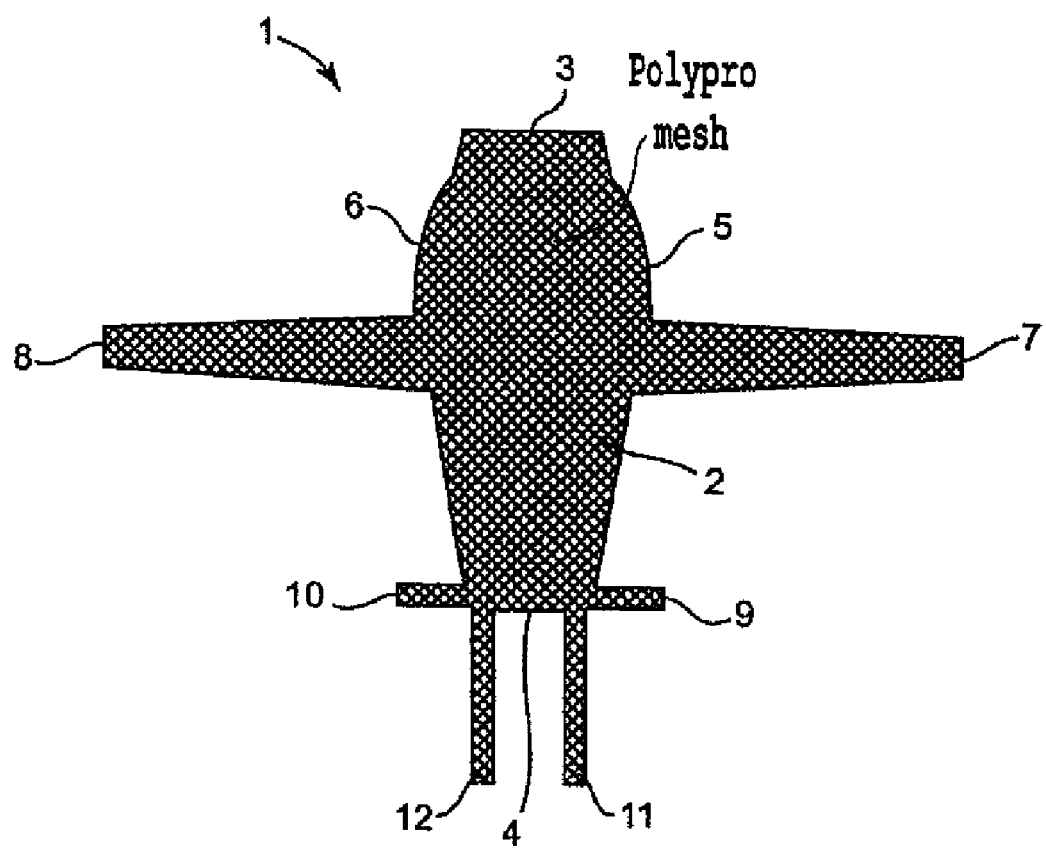
FIG. 5 shows an embodiment of the implant of the present invention.

FIG. 5 shows a preferred embodiment of the implant of the present invention. The implant 1 for repairing posterior pelvic floor pathology includes a central support portion 2 having a plurality of arms. The central portion has an anterior end 3, a posterior end 4, and two lateral ends opposite each other, 5 and 6. The implant preferably comprises a first pair of arms, 7 and 8, extending laterally from about the middle of the central support portion 3. The implant also preferably comprises a second pair of arms, 9 and 10, extending laterally from near the posterior end 4 of the central support portion 1. The implant also preferably comprises a pair of appendages 11 and 12 extending in a posterior direction from the posterior end of the central support portion.

Figure 6:
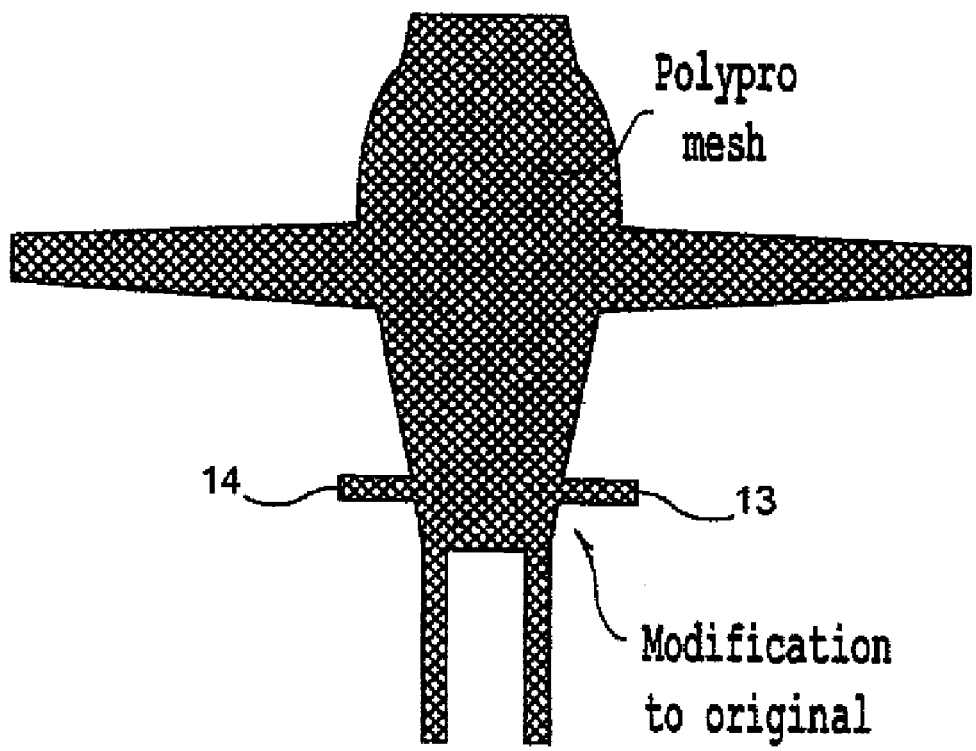
FIG. 6 shows another embodiment of the implant of the present invention.

FIG. 6 shows a preferred modification of the implant of the present invention in which the second pair of arms 13 and 14 are in a slightly more craniad position.

FIGS. 7-34 show alternative embodiments of the implant of the present invention.

Figure 7:
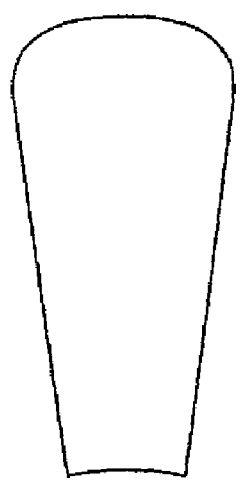
Figure 8:
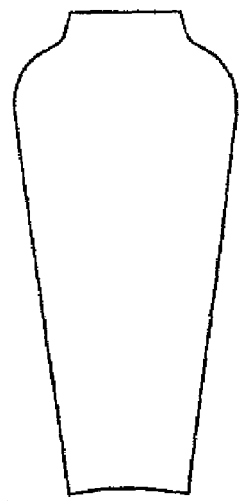
Figure 9:
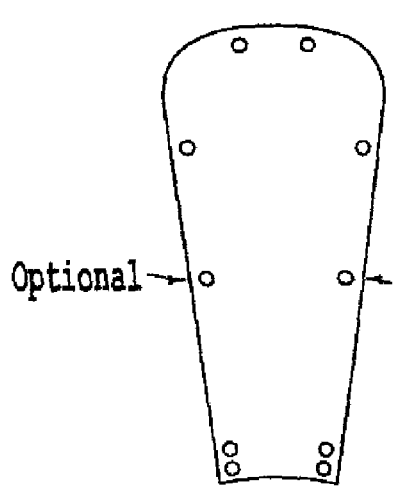
Figure 10:
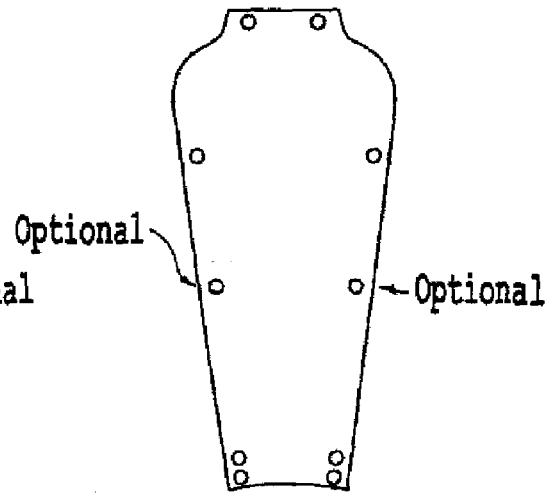
Figure 11:
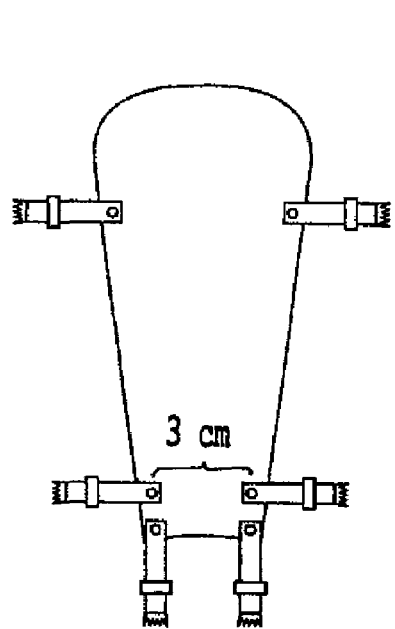
Figure 12:
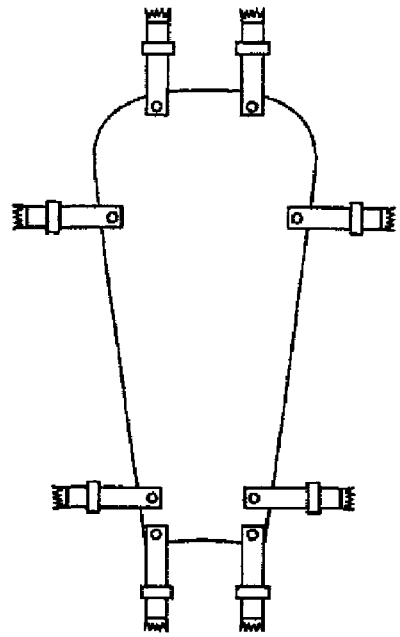
Figure 13:
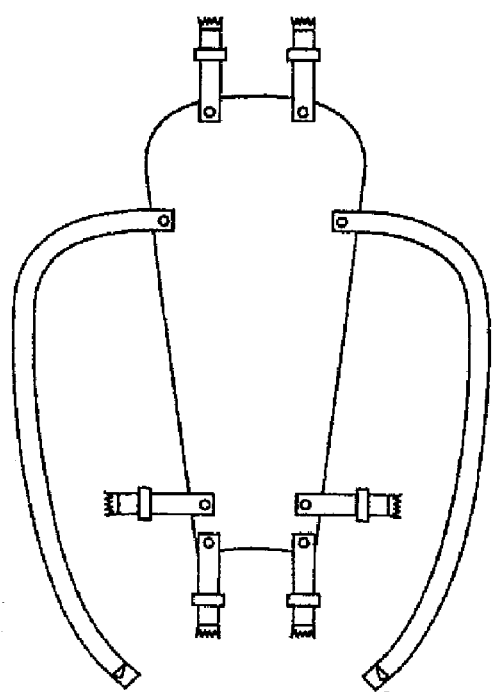
Figure 14:
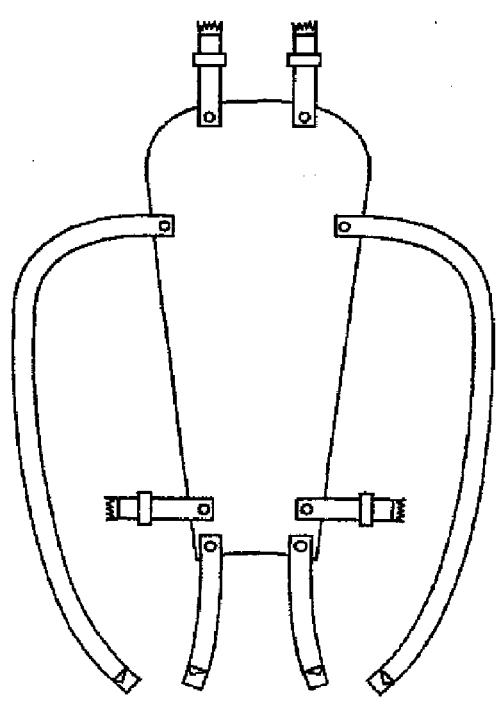
Figure 19:
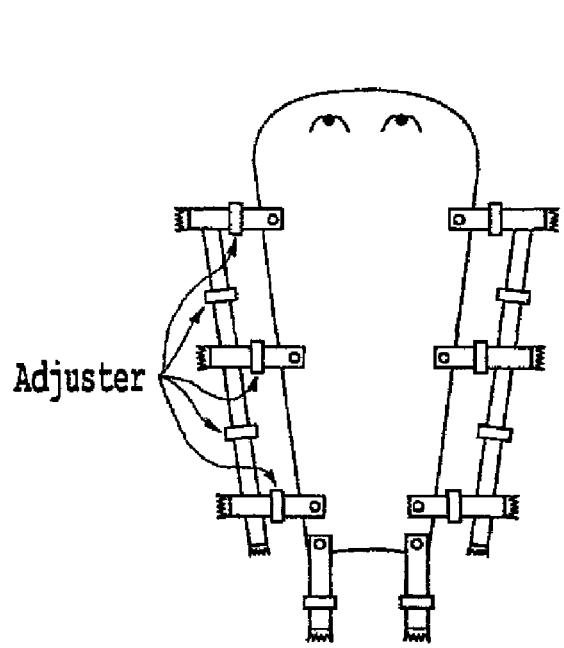
Figure 20:
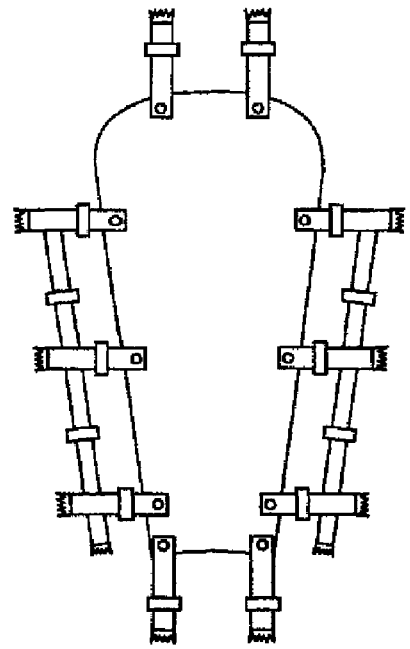
Figure 21:
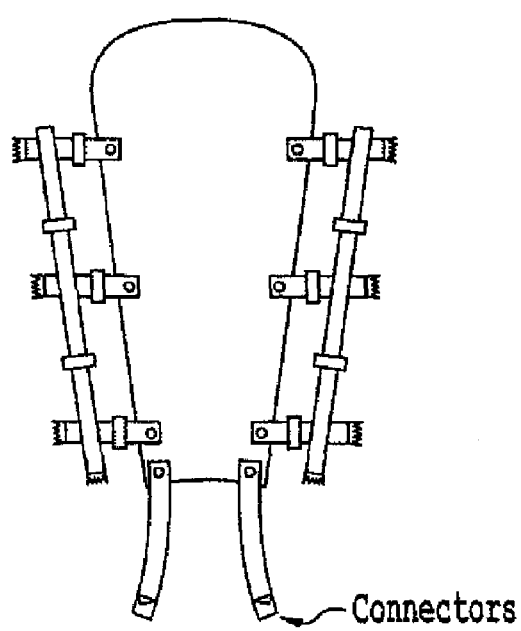
Figure 22:
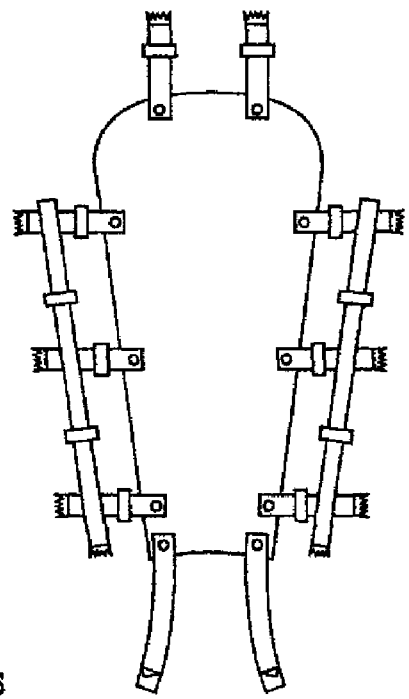
Figure 23:
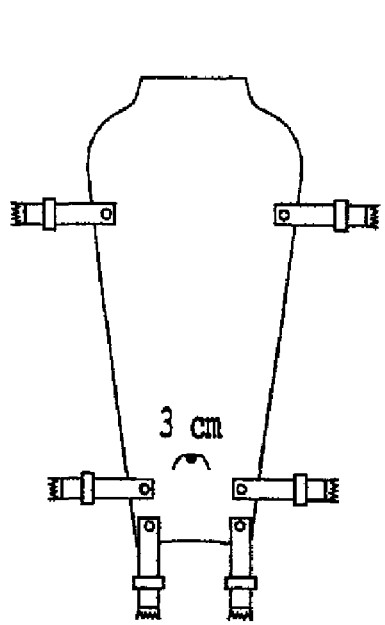
Figure 24:
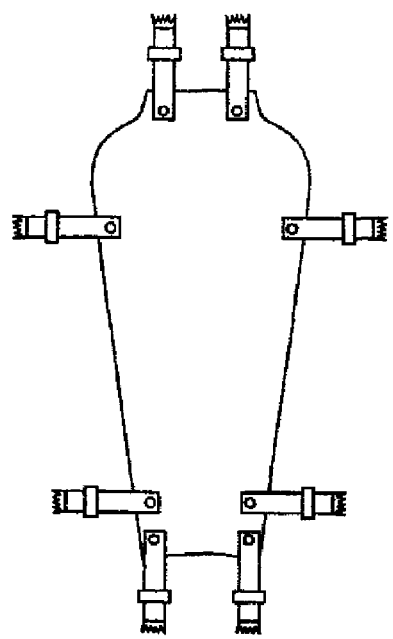
Figure 25:
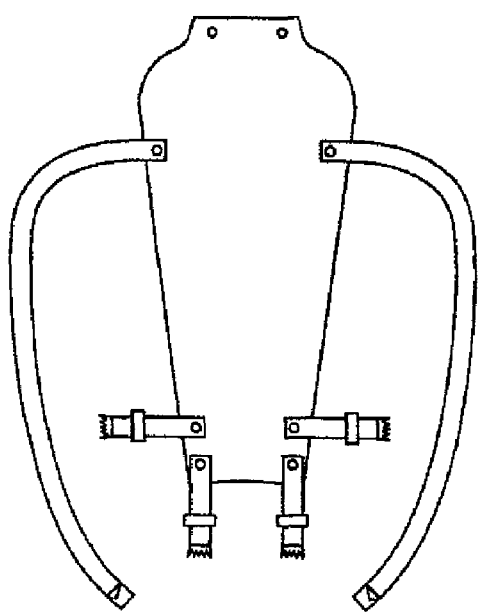
Figure 26:
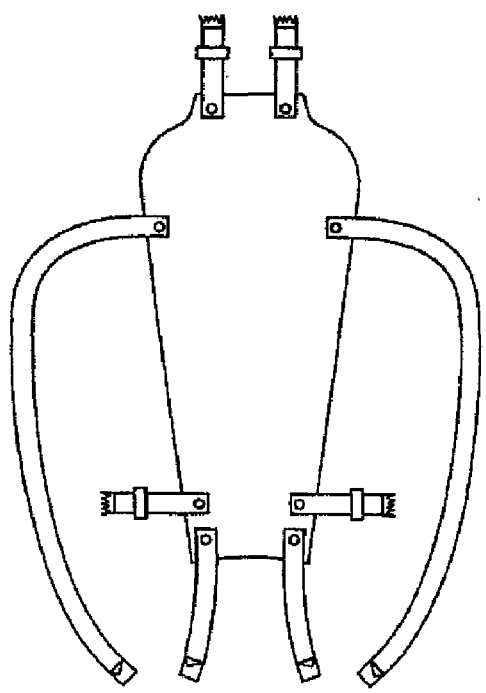
Figure 27:
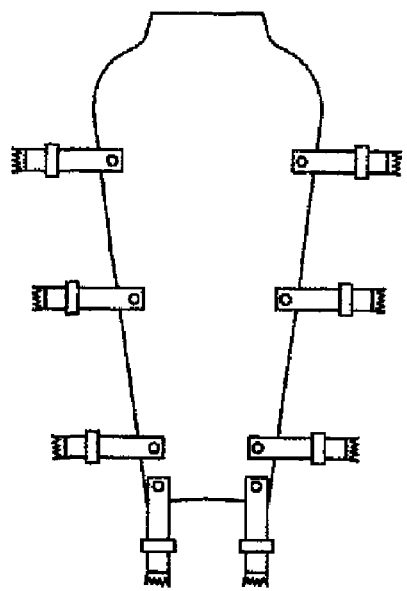
Figure 28:
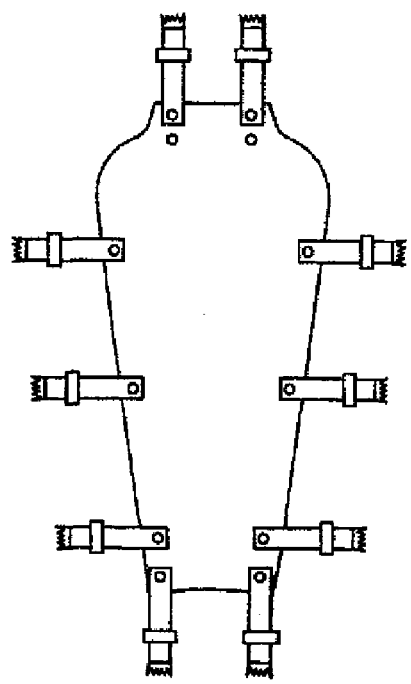
Figure 29:
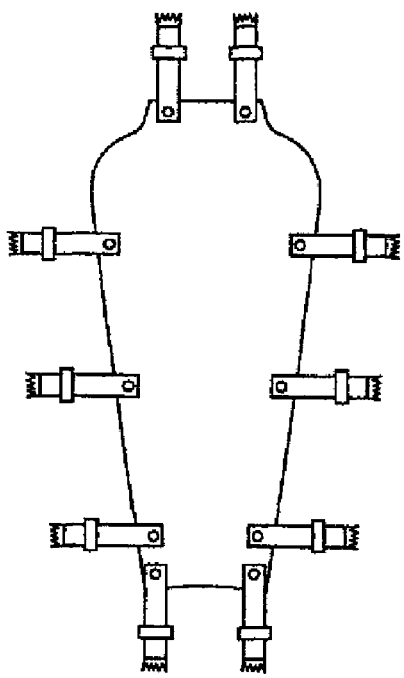
Figure 30:
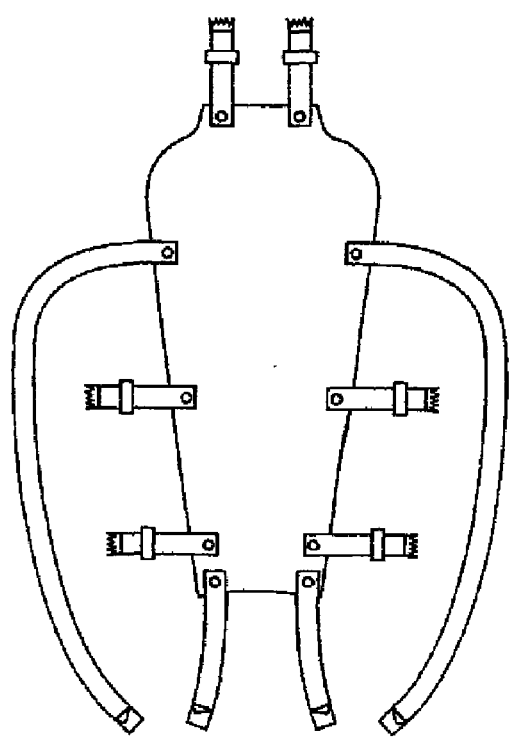

FIGS. 7 and 8 show modifications in the shape of the central support portion. FIGS. 9 and 10 show alternative connection sites for attachment of the arms of the implant device. The arms may be attached via rivets or by other methods known in the art. The arms may alternatively be formed as a single piece along with the central support portion.

The non-exhaustive listing of alternative embodiments all share common functionality in repairing pelvic floor pathology, but may be adapted for the needs of a particular patient. For example, the superior arms coming off the square or rounded part of the central mesh support may be a suitable adaptation to provide an attachment of the mesh to the under side of the apical portion of the vagina. The substantially squared most anterior portion of the mesh may be a suitable adaptation to provide apical support. The rounded mesh that is posterior to the square and above the superior arms may be a suitable adaptation for treatment of enterocele. The superior side arms may be a suitable adaptation for attachment to the sacrospinous ligament. The center body of the mesh may be suitably adapted for treatment of a variety of conditions, including rectocele and rectal prolapse. The optional midarms may be a suitable adaptation for attachment to the arcus tendineus rectovaginalis at midline for additional support.

In a preferred embodiment, the horizontal lower arms may be a suitable adaptation for attachment to the ischial tuberosities and the connective tissue of the perineal body which extends 2 to 4 cm cephalad from the hymenal ring along the posterior vaginal wall. Such an embodiment is especially suitable for treatment of collapsing perineal body, anal incontinence, and rectal prolapse. The lower arms may be suitable adaptations for lateral support to prevent the mesh support portion from twisting and for providing additional support to the rectum and the anus for the treatment of anal incontinence and rectal prolapse, for example.

FIGS. 19-22 and 31-34 show embodiments of the present invention having lateral support structures connecting the arms of the device. Such lateral support structures form a neo-arcus tendineous rectalis to allow for better distribution of tension and more secure placement in anatomic locations lacking sufficient tissue to anchor the present apparatus.

FIGS. 35 and 36 show embodiments of the arms of the present invention. The arms may be of any configuration effective to allow attachment to the appropriate anatomic location. A preferred embodiment is a type 1 arm having a rivet to effect connection to the mesh support with a connector distal to the rivet for attachment to a needle, for example. Another preferred embodiment is the type 2 arm having a rivet to effect connection to the mesh support and a tissue anchor distal to the rivet. Such tissue anchors are alternative methods for attachment to the appropriate anatomical structure. An arm of the present invention may comprise an adjuster located at a position between an end of the arm that attaches to the mesh support and the end of the arm distal to the end that attaches to the mesh support. The adjuster, an example of which is seen in FIG. 36, would allow for adjustment of the length of the arm to allow for a more effective attachment.

FIG. 37 shows an embodiment of a re-connectable tip for the connection of the arm to the central support portion.

Figure 38:
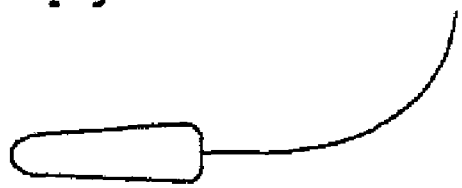
FIGS. 38-40 show embodiments of the implanting device of the present invention.
Figure 39:
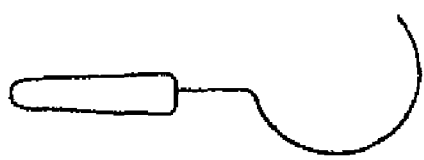
Figure 40:

FIG. 38 shows a preferred embodiment of the implanting device 12 of the present invention. The device comprises a handle and a needle. The needle is curved to allow use in the present operation. The needle comprises a reattachable tip. Such reattachable tip is adapted to allow for atramautic passage of said needle through tissue of a patient, if desired. FIGS. 39 and 40 show alternative embodiments of the implanting device of the present invention.

Figure 41:
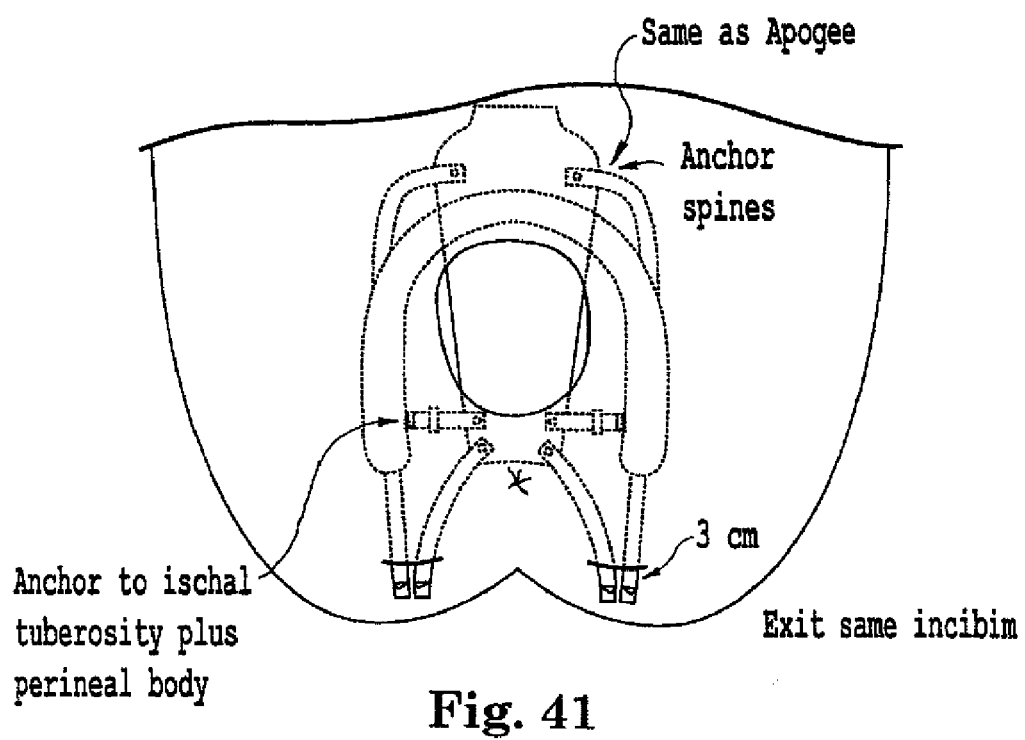
FIG. 41 shows an embodiment of the present implant as disposed in the treatment of posterior pelvic floor pathology.

FIG. 41 illustrates the present implant disposed in a position to treat rectocele or other pelvic floor pathology. The present invention comprises a method for treating rectocele by use of a implant. In order to place the present implant into a therapeutically effective location, the patient is initially placed under general anesthesia. The patient is placed into a dorsal lithotomy position, or otherwise positioned to allow adequate access to the relevant anatomy. An initial vaginal incision is made in order to gain access to the vaginal vault. A first and second small stab incisions are made on each side of the anus, approximately 3 cm lateral and 3 cm posterior to the anus. Implanting device 12 is passed through said first stab incision and pass lateral and parallel to the rectum toward the ischial spine. The tip of the needle should be palpated in front of the ischial spine, at which point the levator muscle is penetrated and the needle is advanced toward the vaginal vault. The tip of the needle is then guided to exit the vaginal incision. These steps are repeated on the contralateral side, with an implanting device needle being passed from the second small stab incision to the vaginal incision.

Following passing of needles of said implant devices to the vaginal incision, arms 7 and 8 are attached to the ends of said needles. The handle of said implant devices are manipulated by the surgeon, pulling the device with the attached arm of the implant back through the stab incision. A first arm is extended through the skin, followed in turn by a second. This causes the implant to be placed exterior the vaginal wall in a position to provide support for the rectocele. Other methods of placing the present apparatus are within the scope of the present invention.

With the described placement of the apparatus of the present invention, Level 2 support for the rectocele is provided. In addition, placement of the implant in a way that supports the detached perineal bodies results in Level 3 support that very nearly approximates a normal condition.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treating pelvic floor pathology comprising providing level 2 and level 3 support for a prolapsed tissue by placement of an apparatus for pelvic floor repair comprising a central support portion and a plurality of arms, the arms including:
   (1) a first pair of arms extending laterally from about a middle or upper half of the central support portion,
   (2) a second pair of arms extending laterally from near a posterior end of the central support portion, and
   (3) a third pair of arms extending in a posterior direction from the posterior end of the central support portion,
the method comprising:
   placing the central support portion to treat a rectocele or rectal prolapse condition,
   extending a first arm of the first pair of arms through a tissue path leading to a first external skin incision approximately 3 centimeters lateral to and 3 centimeters posterior to the anus on a first side of the patient, extending a second arm of the first pair of arms through a tissue path leading to a second external incision on a second side of the patient, and
   attaching each arm of the second pair of arms to an ischial tuberosity and connective tissue of a perineal body.

2. The method according to claim 1 comprising treating one or more of rectocele, posterior enterocele, anal incontinence, rectal prolapse, collapsing perineal body; providing apical support; or providing pudendal nerve stabilization.

3. The method according to claim 1 comprising supporting a perineal body.

4. The method according to claim 1 comprising extending a first arm of the third pair of arms through a tissue path leading to the first external skin incision approximately 3 centimeters lateral and 3 centimeters posterior to the anus on the first side of the patient, extending a second arm of the third pair of arms through a tissue path leading to the second external incision on the second side of the patient.

5. The method according to claim 4 wherein the apparatus further comprising a set of superior arms, and the method comprises attaching each of the superior arms to a sacrospinous ligament.

6. The method according to claim 1 wherein the apparatus further comprises a set of superior arms, and the method comprises attaching each of the superior arms to a sacrospinous ligament.

7. A method of treating pelvic floor pathology comprising providing level 2 and level 3 support for a prolapsed tissue by placement of an apparatus for pelvic floor repair comprising a central support portion and a plurality of arms, the plurality of arms including:
   (1) a first pair of arms extending laterally from about a middle or upper half of the central support portion,
   (2) a second pair of arms extending laterally from near a posterior end of the central support portion, and
   (3) a third pair of arms extending in a posterior direction from the posterior end of the central support portion,
the method comprising attaching each arm of the second pair of arms to an ischial tuberosity and connective tissue of a perineal body.

* * * * *